United States Patent [19]

Bhise et al.

[11] 4,437,938

[45] Mar. 20, 1984

[54] PROCESS FOR RECOVERING ETHYLENE OXIDE FROM AQUEOUS SOLUTIONS

[75] Inventors: Vijay S. Bhise, Bloomfield, N.J.; Robert Hoch, Ridgewood, N.Y.

[73] Assignee: The Halcon SD Group, Inc., New York, N.Y.

[21] Appl. No.: 284,153

[22] Filed: Jul. 17, 1981

[51] Int. Cl.³ ............... B01D 3/34; C07D 301/32
[52] U.S. Cl. ............... 203/14; 203/42; 203/43; 203/47; 203/49; 203/70; 549/541
[58] Field of Search ............ 260/348.37; 203/43, 203/68, 70, 67, 14, 49, 42, 91; 422/256–260; 196/14.52; 210/634, 511; 202/169; 549/541

[56] References Cited

U.S. PATENT DOCUMENTS

| | | |
|---|---|---|
| 1,805,751 | 5/1931 | Auerbach . |
| 2,771,473 | 11/1956 | Courter ............... 260/348.37 |
| 3,265,593 | 8/1966 | Leis et al. ............... 203/63 |
| 3,418,338 | 12/1968 | Gilman et al. ............... 260/348.37 |
| 3,806,619 | 4/1974 | Zosel ............... 426/478 |
| 3,964,980 | 6/1976 | Ozero ............... 203/42 |
| 3,969,196 | 7/1976 | Zosel ............... 203/49 |
| 4,134,797 | 1/1979 | Ozero ............... 203/75 |
| 4,250,331 | 2/1981 | Shimshick ............... 562/485 |
| 4,253,948 | 3/1981 | Hardman et al. ............... 210/634 |
| 4,349,415 | 9/1982 | De Flippi et al. ............... 203/14 |

FOREIGN PATENT DOCUMENTS

| | | |
|---|---|---|
| 1290117 | 9/1972 | United Kingdom . |
| 1388581 | 3/1975 | United Kingdom . |
| 2032789 | 5/1980 | United Kingdom ............... 203/49 |
| 2059787 | 4/1981 | United Kingdom . |

OTHER PUBLICATIONS

Stahl et al., Angew. Chem. Int. Ed. Engl. 17, pp. 731–738, (1978).
J. Am. Chem. Soc., 58, 1099, (1954), Francis, A. W.

*Primary Examiner*—Wilbur L. Bascomb, Jr.
*Attorney, Agent, or Firm*—William C. Long; Riggs T. Stewart; Harold N. Wells

[57] ABSTRACT

Ethylene oxide is recovered from aqueous solutions by extracting with carbon dioxide in the near-critical or super-critical state, thereby selectively removing the ethylene oxide from water, and thereafter recovering ethylene oxide from the carbon dioxide by distillation or other suitable means.

6 Claims, 2 Drawing Figures

PROCESS FOR RECOVERING ETHYLENE OXIDE FROM AQUEOUS SOLUTIONS

PRIOR ART

The invention relates to the recovery of ethylene oxide from aqueous solutions. In particularly useful aspect, the invention relates to the separation of ethylene oxide from aqueous solutions formed when the gaseous effluent from the vapor-phase catalyzed oxidation of ethylene is contacted with a recirculating aqueous solution. Typically, these solutions are separated by distillation, at a substantial cost for the energy required.

The effluent from the oxidation of ethylene, which is typically carried out at 10–40 kg/cm$^2$ gauge and 200°–400° C. is contacted with water to absorb the ethylene oxide from the gases, which can then be recycled to the oxidation reactor. This absorption in water is typically carried out at a pressure near that of the reaction and the ethylene oxide-rich aqueous stream which results is at a fairly low temperature, about 30°–100° C., and is quite dilute in ethylene oxide, typically about 0.5–5%. Recovery of pure ethylene oxide from water is an energy-intensive process if done by conventional distillation or the combination of distillation and water reabsorption as taught for example in U.S. Pat. Nos. 3,418,338, 3,964,980, and 4,134,797. A substantial reduction of the energy required can be achieved by the extraction process of our invention.

The use of normally gaseous materials in their near-critical or super-critical states as solvents has been known, especially in connection with the separation of hydrocarbon mixtures, such as is disclosed in U.S. Pat. No. 1,805,751. Interest in such separations has revived recently since extractions with near or super-critical fluids may take place at relatively low temperatures and with the expenditure of less energy than is used by more conventional methods of separation. The terms "near-critical" and "super-critical" are well known to those skilled in the art. For purposes of the present invention, these may include reduced temperatures in the range of about 0.6–1 (i.e. near-critical) and about 1–3 (i.e. super-critical).

A general discussion in Angew. Chem. Int. Ed. Engl. 17, p. 731–738 (1978) of the possibility of recovering various organic compounds by super-critical gases mentions the pyrones, which are high molecular weight epoxides, but are not oxirane compounds. Oxirane compounds, such as ethylene oxide, are not mentioned.

The use of (near) super-critical fluids for separating compounds from aqueous solutions has been less commonly discussed. For example, in U.S. Pat. No. 3,969,196 it is shown that ethylene is not capable of absorbing ethylene glycol and ethyl alcohols from their aqueous solutions while higher alcohols can be recovered. Francis, in J. Am. Chem. Soc., 58, p. 1099 (1954) disclosed that carbon dioxide near its critical point has only slight ability to absorb ethylene glycol and water but is completely miscible with ethyl alcohol. No mention of ethylene oxide was made.

In British Pat. No. 1,290,117 the use of carbon dioxide to extract caffeine from aqueous solutions suggests that moist carbon dioxide in the super-critical state has the properties of a polar fluid and is able to take up polar compounds, such as caffeine.

Recovery of acrylic acid from aqueous solutions with carbon dioxide is disclosed in U.S. Pat. No. 4,253,948, which features the rejection of water taken up in the carbon dioxide by the formation of hydrates.

Various agricultural products have been treated with super-critical carbon dioxide, as for example in U.S. Pat. Nos. 3,806,619, 3,843,824, 3,939,281, and 3,923,847 and British Pat. No. 1,388,581.

The recovery of carboxylic acids from dilute aqueous solutions of their alkali metal salts with super-critical carbon dioxide is disclosed in U.S. Pat. No. 4,250,331. The carbon dioxide reacts with the salt to form the acid, which is extracted by carbon dioxide. It is suggested that other, more polar, super-critical fluids may be added as needed to improve the solubility of certain acids in carbon dioxide.

Published British application GB No. 2,059,787A discloses a process for separating organic compounds, particularly water-miscible oxygenated hydrocarbons, from aqueous solutions with super-critical carbon dioxide and subsequent fractionation featuring the use of vapor recompression to minimize the energy requirements for the separation of the organic compounds from carbon dioxide. Although alcohols, acids, aldehydes, esters, and ketones are mentioned generally, the application of such a process to ethylene oxide is not suggested.

Large amounts of water are required to absorb ethylene oxide, which has a large activity coefficient in an ethylene oxide-water mixture. Improved processes for recovering ethylene oxide have been sought, particularly since the distillation of dilute aqueous solutions has become more costly. It has now been found that the extraction of ethylene oxide by (near) super-critical fluids, specifically carbon dioxide, is feasible and provides advantages over prior art recovery methods.

SUMMARY OF THE INVENTION

Ethylene oxide is recovered from aqueous solutions, especially those formed by the contacting of the gaseous effluent of the vapor-phase catalyzed oxidation of ethylene with recirculating aqueous streams, by contacting such aqueous solutions with solvent in the super-critical or near critical state, specifically carbon dioxide. The conditions of the contacting are chosen to selectively extract ethylene oxide from water into the solvent. Thereafter, the ethylene oxide-rich solvent is separated from the ethylene oxide-lean aqueous solution and the ethylene oxide recovered from the solvent by distillation or other suitable means.

In a preferred embodiment, carbon dioxide at a temperature in the range of about 0°–100° C. and a pressure in the range of about 35–300 kg/cm$^2$ gauge is brought into contact with an aqueous ethylene oxide solution containing about 0.1–10 mol % ethylene oxide. The carbon dioxide selectively extracts ethylene oxide to an extent determined by the operating conditions, typically above 90% is removed from the aqueous solution. The ethylene oxide-rich carbon dioxide is physically separated from the depleted aqueous solution, which remains a distinct liquid phase and thereafter the ethylene oxide-rich solvent is subjected to changes in temperature and/or pressure such that ethylene oxide may be recovered. In one embodiment, the pressure of the ethylene oxide-rich carbon dioxide will be reduced to about 30–75 kg/cm$^2$ gauge and the carbon dioxide distilled off and recycled to recover additional ethylene oxide.

DESCRIPTION OF THE PREFERRED EMBODIMENTS

The use of (near) super-critical fluids such as carbon dioxide is especially useful in the recovery of ethylene oxide from the aqueous solutions which commercial ethylene oxide plants usually produce. Ethylene is oxidized in the vapor-phase by passing it along with molecular oxygen and diluents, such as nitrogen or methane, over a supported silver catalyst. The ethylene oxide typically is recovered by absorbing it in water.

Figure 1:
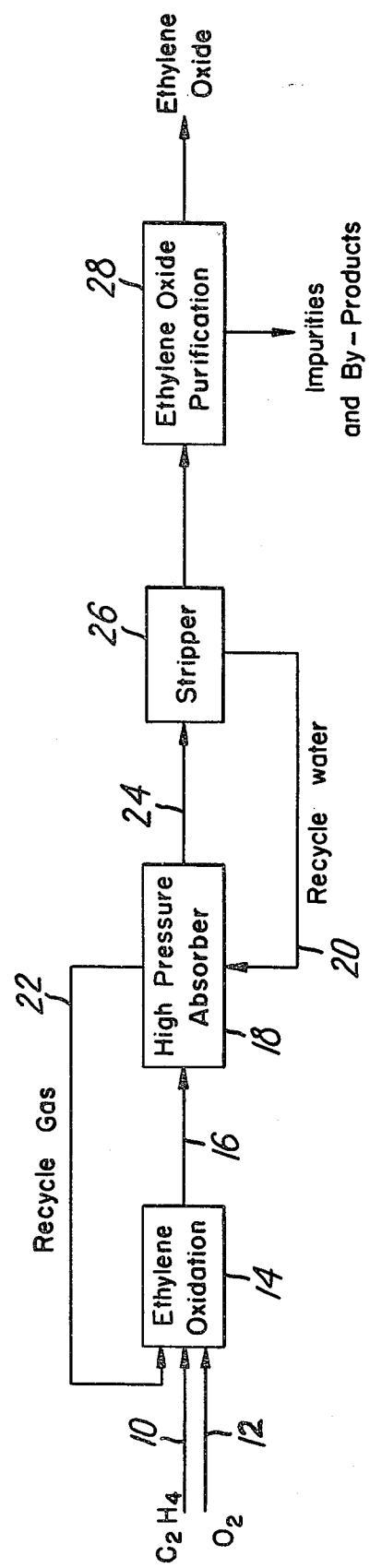
FIG. 1 is a block diagram illustrating the process for catalytic oxidation of ethylene to ethylene oxide and its recovery.

The conventional ethylene oxide process is illustrated schematically in FIG. 1. Ethylene (10) and oxygen (12) are fed to a catalytic oxidation reactor (14) employing a supported silver catalyst, which is disposed inside tubes surrounded by a heat transfer fluid used to remove the heat of reaction. Only a fraction of the ethylene is converted to ethylene oxide in each pass through the reactor and consequently a significant amount of ethylene is usually recycled, along with diluent gases, such as nitrogen or methane, to the reactor. Gases leaving the reactor via line 16 at about 10-40 kg/cm$^2$ gauge and 200°-400° C. are passed to a high pressure absorber (18) where they meet a recycling water stream (20) and are quenched and the ethylene oxide is absorbed, along with carbon dioxide and various impurities produced in the oxidation reactor. The gases which are not absorbed are separated from the aqueous ethylene oxide solution and recycled via line 22 to the reactor (14). The ethylene oxide-rich solution is sent via line 34 to a stripper (26) where ethylene oxide is separated and the lean water recycled via line 20 to the high pressure absorber (18). After this, the gaseous ethylene oxide may be absorbed again in a suitable solvent such as water or ethylene carbonate and separated from various impurities, by methods which are shown in this figure generally as purification (28), but which may include those in the U.S. patents previously mentioned. The final product may be substantially pure ethylene oxide as indicated, or alternatively, a mixture of ethylene oxide and carbon dioxide could be produced suitable for preparation of ethylene carbonate.

Figure 2:
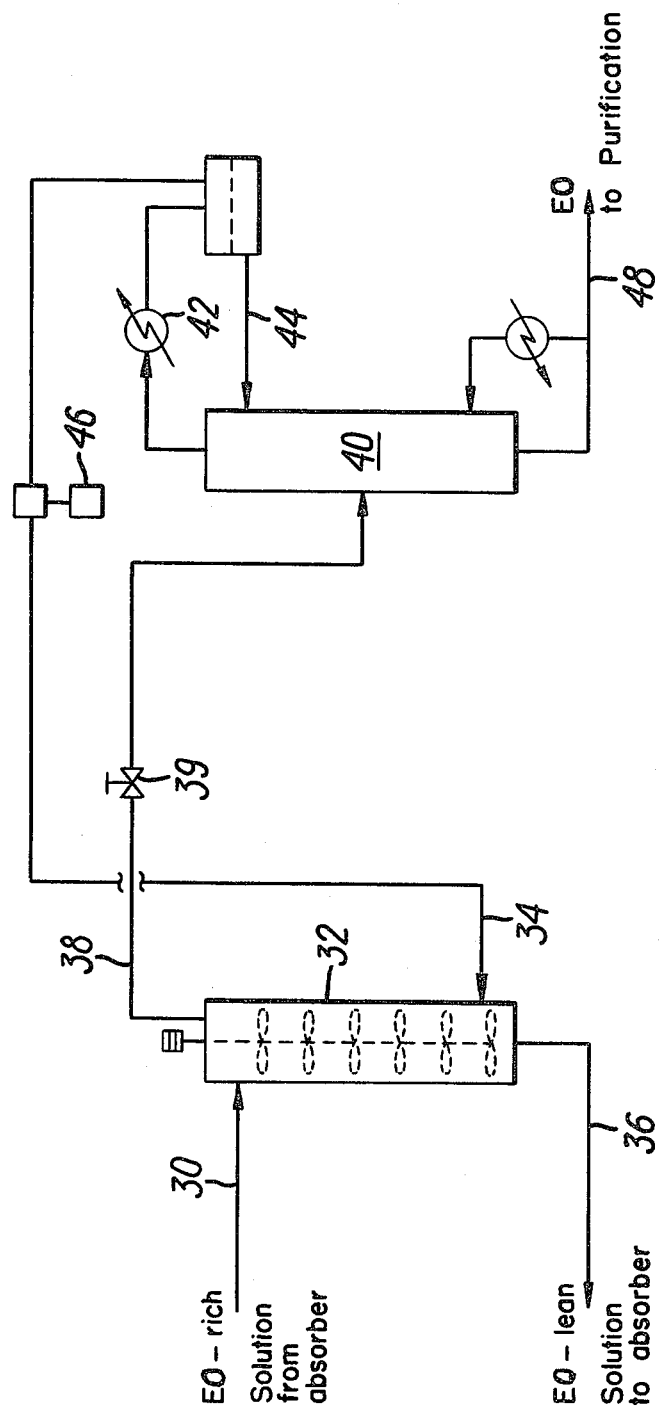
FIG. 2 shows an application of the process of the invention to the recovery of ethylene oxide from high pressure aqueous solutions.

FIG. 2 illustrates one embodiment of the invention. An aqueous solution containing about 0.1 mol % (max. about 10 mol %) ethylene oxide is available from the high pressure absorber (18) of FIG. 1 at about 10-40 kg/cm$^2$ gauge and 50°-100° C. For purposes of this example, the pressure is about 20 kg/cm$^2$ gauge and the temperature 60° C. Rather than stripping the ethylene oxide as shown in the conventional process of FIG. 1, the aqueous solution is supplied via line 30 to a mixing column 32 where it passes in countercurrent manner against a stream (34) of carbon dioxide at near critical or super-critical condition, selected so as to selectively extract above 90% of the ethylene oxide. Smaller fractions could be extracted, but less complete removal of ethylene oxide may not be economically advantageous. The critical conditions for carbon dioxide are 31° C. and 75.1 kg/cm$^2$ gauge so that the extraction will be carried out at temperatures in the range of about 0°-100° C. and 35°-300 kg/cm$^2$ gauge. In this example, the pressure is about 88 kg/cm$^2$ gauge and the temperature about 32° C. By proper selection of the amount of carbon dioxide and the operating pressure and temperature, substantially all of the ethylene oxide can be extracted while the bulk of the water is rejected. In this example, about 35 mols of carbon dioxide per mol of ethylene oxide is used and substantially all of the ethylene oxide is absorbed. Despite the relatively large amount of water, less than about 1% will be picked up by the carbon dioxide by absorption, entrainment and the like under the optimum conditions for extraction of ethylene oxide. The presence of this water is neglected for purposes of the present example. Thus, a substantially complete separation is made. The equipment employed for this contacting will be familiar to those skilled in the art and may include staged mixing in a sequence of vessels, but typically a stirred mixing column (as shown) or a tower equipped with trays or packing would be used.

The lean aqueous solution is returned to the absorber via line 36 after the net production of ethylene oxide has been removed. The carbon dioxide rich in ethylene oxide (about 2.9 mol %) is sent via line 38 from the contacting stage (32) to a separation stage (40) for removal of the ethylene oxide. The separation may be carried out by various procedures, depending particularly upon the operating conditions. The figure illustrates one suitable method for making the separation. The ethylene oxide-carbon dioxide mixture is passed to a distillation column (40) where the two constituents are separated, with the carbon dioxide being condensed in exchanger 42 and returned as reflux via line 44 and sent via line 34 and compressor 46 to the extraction column 32 and ethylene oxide plus some carbon dioxide and impurities and by-products being sent via line 48 to further purification steps. It is the intention of the figures to illustrate the situation in which the operating pressure is reduced across a valve 39 (although an expander could be used to recover power) so that the absorption capacity of the carbon dioxide is reduced and ethylene oxide can be separated. The operating pressure for the distillation would be selected to remain near the critical value to take advantage of the reduced latent heat of vaporization, but could be in the range of 30-75 kg/cm$^2$. For this example, the pressure is about 73 kg/cm$^2$ gauge. The pressure may be about 70-75 kg/cm$^2$ gauge if pure carbon dioxide is used and the operating temperature at the bottom of the column would be less than about 50° C. (depending upon pressure) and at the top 0°-50° C. For this example, the bottom temperature is about 43° C. and the top temperature is about 30° C.

Under the conditions described it may be difficult to economically condense carbon dioxide without refrigeration and adulterant gases, such as propane or butane, which have higher critical temperatures than carbon dioxide, may be used to increase the critical temperature and pressure of the vapor mixture at the top of the column, thus making possible more economical condensation.

Other operating techniques are considered within the scope of the invention, for instance the method disclosed in GB No. 2,059,787A in connection with the separation of other compounds from carbon dioxide. It is also possible to adjust the temperature of the ethylene oxide-rich stream to reduce the ability of the carbon dioxide to absorb the ethylene oxide and, thus, permitting the separation to be made. Broadly, speaking, the selection of the method employed will be made based on the costs of each method as affected by the physical properties which are associated with the ethylene oxide-(near) super-critical fluid system being considered.

The application of the invention need not be not confined to the high pressure solution formed from the oxidation reactor effluent as shown in FIG. 2 and discussed above. Other aqueous solutions of ethylene oxide may be treated in the same manner, as for example the solution produced when the high pressure solution is stripped of ethylene oxide, which is then reabsorbed in water in conventional ethylene oxide recovery. Those skilled in the art will recognize there are various aqueous solutions to which the extraction of ethylene oxide by (near) super-critical carbon dioxide may be applied.

What is claimed is:

1. A process for recovering ethylene oxide from aqueous solutions comprising:
   (a) contacting said aqueous solution of ethylene oxide with a solvent comprising carbon dioxide in the near-critical or super-critical state to selectively absorb ethylene oxide relative to water and;
   (b) separating the ethylene oxide-containing carbon dioxide of (a) from the ethylene oxide-depleted aqueous solution and thereafter;
   (c) recovering the ethylene oxide from the separated ethylene oxide-containing carbon dioxide of (b).

2. A process of claim 1 wherein said recovery process of (c) comprises reducing the pressure of step (b) and distilling the carbon dioxide from the ethylene oxide.

3. A process of claim 2 wherein the pressure of steps (a) and (b) is about 35–300 kg/cm$^2$ gauge and the pressure of step (c) is about 30–75 kg/cm$^2$ gauge.

4. A process of claim 1 wherein an adulterant gas is included during recovery step (c) to increase the critical temperature of the mixture.

5. In the process for recovering ethylene oxide from the gaseous effluent of the vapor-phase catalyzed oxidation of ethylene where said ethylene oxide is absorbed from said gaseous effluent into an aqueous recirculating stream and thereafter recovered from the ethylene oxide-rich aqueous stream, the improvement which comprises contacting said ethylene oxide-rich aqueous steam with carbon dioxide in the near-critical or super critical state to selectively absorb the ethylene oxide.

6. A process of claim 5 wherein the pressure of said carbon dioxide contacting is about 35–300 kg/cm$^2$ and the temperature is about 0°–100° C.

* * * * *